US009532719B2

(12) United States Patent
Shida

(10) Patent No.: US 9,532,719 B2
(45) Date of Patent: Jan. 3, 2017

(54) FLUORESCENCE ENDOSCOPE APPARATUS

(71) Applicant: OLYMPUS CORPORATION, Tokyo (JP)

(72) Inventor: Hiromi Shida, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 391 days.

(21) Appl. No.: 14/154,243

(22) Filed: Jan. 14, 2014

(65) Prior Publication Data

US 2014/0128680 A1 May 8, 2014

Related U.S. Application Data

(63) Continuation of application No. PCT/JP2012/067740, filed on Jul. 11, 2012.

(30) Foreign Application Priority Data

Jul. 22, 2011 (JP) .................................. 2011-160886

(51) Int. Cl.
  *A61B 1/06* (2006.01)
  *A61B 1/04* (2006.01)
  *A61B 5/00* (2006.01)
  (Continued)

(52) U.S. Cl.
  CPC ......... *A61B 5/0071* (2013.01); *A61B 1/00009* (2013.01); *A61B 1/043* (2013.01);
  (Continued)

(58) Field of Classification Search
  CPC ... A61B 1/00009; A61B 1/043; A61B 1/0638; A61B 1/0661; G02B 21/16; G02B 21/244; G02B 23/2469; G06T 5/50
  (Continued)

(56) References Cited

U.S. PATENT DOCUMENTS 5,749,830 A * 5/1998 Kaneko .............. A61B 1/00082
                                                         348/E5.038
6,364,829 B1 * 4/2002 Fulghum ............ A61B 1/00009
                                                         600/160
(Continued)

FOREIGN PATENT DOCUMENTS

JP          62-247232 A       10/1987
JP          08-317915 A       12/1996
                 (Continued)

OTHER PUBLICATIONS

Extended Supplementary European Search Report dated Apr. 30, 2015 from related European Application No. 12 81 6953.9.
(Continued)

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

A fluorescence endoscope apparatus includes a light source that radiates excitation light and reference light onto an examination target; a fluorescence-image generating portion that generates a fluorescence image by capturing fluorescence generated at the examination target due to irradiation with the excitation light; a reference-image generating portion that generates a reference image by capturing return light that returns from the examination target due to irradiation with the reference light; a division-image generating portion that generates a division image by dividing the fluorescence image generated by the fluorescence-image generating portion by the reference image generated by the reference-image generating portion; and a corrected-image generating portion that generates a corrected image based on the division image and the fluorescence image, wherein the corrected-image generating portion generates a corrected image in which a region that has relatively high luminance and that the division image and the fluorescence image have in common is emphasized.

14 Claims, 7 Drawing Sheets

(51) Int. Cl.
  *G02B 21/16* (2006.01)
  *G02B 21/24* (2006.01)
  *G02B 23/24* (2006.01)
  *A61B 1/00* (2006.01)
  *G06T 5/50* (2006.01)

(52) U.S. Cl.
  CPC .......... *A61B 1/0638* (2013.01); *A61B 1/0661* (2013.01); *G02B 21/16* (2013.01); *G02B 21/244* (2013.01); *G02B 23/2469* (2013.01); *G06T 5/50* (2013.01); *A61B 1/0646* (2013.01); *G06T 2207/10064* (2013.01); *G06T 2207/10068* (2013.01); *G06T 2207/30004* (2013.01)

(58) Field of Classification Search
  USPC .... 600/109, 160, 178, 180, 181; 348/65, 68, 348/70; 382/128, 266
  See application file for complete search history.

(56) References Cited

U.S. PATENT DOCUMENTS

2002/0161282 A1* 10/2002 Fulghum ............ A61B 1/00009
                                                      600/160
2003/0013937 A1    1/2003 Tsujita et al.
2003/0078477 A1*   4/2003 Kang .................... A61B 1/042
                                                      600/178
2004/0148141 A1    7/2004 Tsujita et al.
2010/0245552 A1*   9/2010 Higuchi ............ A61B 1/00096
                                                       348/68

FOREIGN PATENT DOCUMENTS

| JP | 2003-036436 A | 2/2003 |
| JP | 2005-261974 A | 9/2005 |
| JP | 2006-175052 A | 7/2006 |
| JP | 2008-093254 A | 4/2008 |
| JP | 2010-227253 A | 10/2010 |
| JP | 2011-024726 A | 2/2011 |
| WO | 2013/035738 A1 | 3/2013 |

OTHER PUBLICATIONS

International Search Report dated Aug. 7, 2012 issued in PCT/JP2012/067740.

* cited by examiner

CORRECTED IMAGE

FLUORESCENCE ENDOSCOPE APPARATUS

CROSS-REFERENCE TO RELATED APPLICATIONS

This is a continuation of International Application PCT/JP2012/067740, with an international filing date of Jul. 11, 2012, which is hereby incorporated by reference herein in its entirety. This application claims the benefit of Japanese Patent Application No. 2011-160886, the content of which is incorporated herein by reference.

TECHNICAL FIELD

The present invention relates to a fluorescence endoscope apparatus.

BACKGROUND ART

In the related art, there is a known fluorescence endoscope apparatus with which an observation target site that is administered with a fluorescent reagent that preferentially accumulates in a diseased portion, such as cancer cells or the like, is irradiated with excitation light that excites the fluorescent reagent, generating fluorescence, and with which a fluorescence image having high luminance in the diseased portion can be obtained by capturing the generated fluorescence (for example, see Patent Literature 1). The fluorescence endoscope apparatus disclosed in Patent Literature 1 corrects changes in the fluorescence intensity in a fluorescence image, which depends on the observation distance, the observation angle, and so forth, by dividing the fluorescence image, which is based on the intensity of fluorescence generated at the observation target site irradiated with excitation light, by a reference image, which is based on the intensity of return light returning from the same observation target site irradiated with reference light.

CITATION LIST

Patent Literature

{PTL 1}
Japanese Unexamined Patent Application, Publication No. 2006-175052

SUMMARY OF INVENTION

Technical Problem

Because the fluorescent reagent actually accumulates not only in a diseased portion but also in a healthy portion in a small amount, and because, although weaker than the fluorescence from the diseased portion, fluorescence is also detected from the healthy portion, a fluorescence image that has a background over the entire image is acquired. In addition, the reference image is an image that is affected not only by the observation distance and the observation angle, but also by the color characteristics of the examination target and the shape thereof, such as protrusions and depressions. Therefore, for example, when a fluorescence image having a background is divided by a reference image in which the return-light intensity is reduced due to the absorption characteristics, which is a color characteristic of an examination target, a division image in which the fluorescence intensity of the background is amplified is acquired. Also, because an examination target having a complicated shape causes shading due to protrusions and depressions thereof, when a fluorescence image having a background is divided by a reference image in which the return-light intensity is reduced, a division image in which the fluorescence intensity of the background is amplified is acquired. Because of this, even if a fluorescence image is divided by a reference image, as in the fluorescence endoscope apparatus disclosed in Patent Literature 1, the obtained division image ends up being an image that is affected by factors other than the observation distance and the observation angle, such as differences in the absorption characteristics, the shape, and so forth. As a result, even if a diseased portion and a healthy portion are distinguished from each other by setting a threshold for gradation values, the threshold becomes inappropriate when the observation conditions change, and the diseased portion may not be displayed or the background may be displayed brightly, thus making it impossible to reliably identify the diseased portion with high precision.

The present invention provides a fluorescence endoscope apparatus with which a diseased portion can be identified more accurately and with high precision, regardless of the observation conditions and the state (color and shape) of an examination target.

Solution to Problem

The present invention provides a fluorescence endoscope apparatus including a light source that radiates excitation light and reference light onto an examination target; a fluorescence-image generating portion that generates a fluorescence image by capturing fluorescence generated at the examination target due to irradiation with the excitation light from the light source; a reference-image generating portion that generates a reference image by capturing return light that returns from the examination target due to irradiation with the reference light from the light source; a division-image generating portion that generates a division image by dividing the fluorescence image generated by the fluorescence-image generating portion by the reference image generated by the reference-image generating portion; and a corrected-image generating portion that generates a corrected image based on the division image and the fluorescence image, wherein the corrected-image generating portion generates a corrected image in which a region that has relatively high luminance and that the division image and the fluorescence image have in common is emphasized.

In addition, in the present invention described above, it is preferable that a weighting processing portion that performs weighting processing on the division image and the fluorescence image in accordance with the examination target be provided, and that the corrected-image generating portion generate a corrected image based on the division image and the fluorescence image to which weights are assigned by the weighting processing portion.

In the above-described invention, it is preferable that the corrected-image generating portion generate a corrected image by multiplying the division image by the fluorescence image.

In the above-described invention, it is preferable that the corrected-image generating portion generate a corrected image by adding the division image and the fluorescence image.

The above-described invention may be provided with an identifying portion that identifies, based on a predetermined threshold, a region that has a gradation value greater than the threshold in the corrected image.

The above-described invention may be provided with a threshold setting portion that sets the threshold based on an average value of gradation values of individual pixels in the corrected image.

The above-described invention may be provided with an image combining portion that generates a combined image by superimposing the region identified by the identifying portion on the reference image.

DESCRIPTION OF EMBODIMENTS

First Embodiment

A fluorescence endoscope apparatus according to the first embodiment of the present invention will be described below with reference to the drawings.

Figure 1:
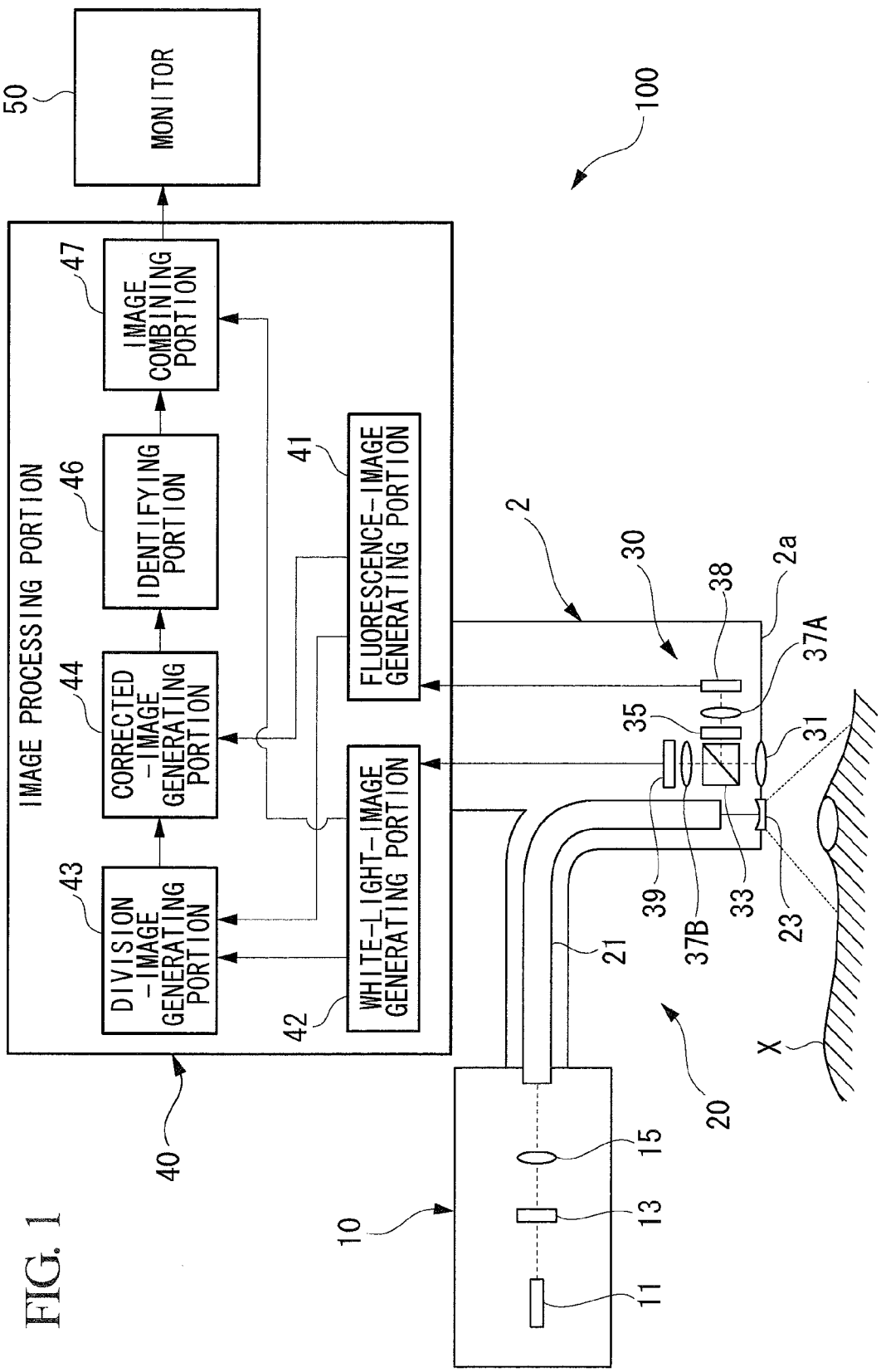
FIG. 1 is a diagram showing, in outline, the configuration of a fluorescence endoscope apparatus according to a first embodiment of the present invention.

As shown in FIG. 1, a fluorescence endoscope apparatus 100 according to this embodiment is provided with a long, thin scope 2 that is inserted into a body cavity; an illuminating unit 20 provided with a light source 10 that emits illumination light that emerges from the distal end 2a of the scope 2; an image acquisition unit 30 that is disposed in the scope 2 and that acquires image information of an observation target site X, which is an examination target; an image processing portion 40 that processes the image information acquired by the image acquisition unit 30; and a monitor 50 that displays the image, the image information, and so forth processed by the image processing portion 40.

The light source 10 is provided with a xenon lamp (Xe lamp) 11 that emits the illumination light; an excitation-light filter 13 that extracts white light containing excitation light from the illumination light emitted from the xenon lamp 11; and a coupling lens 15 that focuses the white light containing the excitation light extracted by the excitation-light filter 13.

The excitation-light filter 13 extracts, for example, white light containing excitation light in a wavelength band of 400 to 740 nm.

In addition, the illuminating unit 20 is provided with a light-guide fiber 21 that is disposed over nearly the entire length of the scope 2 in the longitudinal direction and a spreading lens 23 that is disposed at the distal end 2a of the scope 2.

The light-guide fiber 21 guides the white light containing the excitation light that is focused by the coupling lens 15 to the distal end 2a of the scope 2. The spreading lens 23 spreads out and radiates the white light containing the excitation light, which is guided by the light-guide fiber 21, toward the observation target site X.

The image acquisition unit 30 is provided with an objective lens 31 that collects return light returning from the observation target site X which is irradiated with the white light containing the excitation light from the illuminating unit 20, and a beam splitter 33 that splits the return light collected by the objective lens 31 in accordance with the wavelengths thereof.

The objective lens 31 is disposed at the distal end 2a of the scope 2 beside the spreading lens 23. Of the return light, the beam splitter 33 reflects light having the excitation wavelength or greater (excitation light and fluorescence), and allows the white light (return light) whose wavelength is shorter than the excitation wavelength to pass therethrough.

In addition, this image acquisition unit 30 is provided with an excitation-light cut filter 35 that, of the excitation light and the fluorescence reflected by the beam splitter 33, blocks the excitation light and allows only the fluorescence (for example, near-infrared fluorescence) to pass therethrough; a focusing lens 37A that focuses the fluorescence that has passed through the excitation-light cut filter 35; a focusing lens 37B that focuses the white light that has passed through the beam splitter 33; a fluorescence capturing portion 38 that captures the fluorescence focused by the focusing lens 37A; and a white-light capturing portion 39 that captures the white light focused by the focusing lens 37B.

The excitation-light cut filter 35 allows only the fluorescence in, for example, a wavelength band of 765 to 850 nm, to pass therethrough. The fluorescence capturing portion 38 is, for example, a high-sensitivity monochrome CCD designed for fluorescence, and this fluorescence capturing portion 38 acquires fluorescence image information by capturing the fluorescence. The white-light capturing portion 39 is, for example, a color CCD designed for white light, and is provided with a mosaic filter (not shown). This white-light capturing portion 39 acquires white-light image information by capturing the white light.

The image processing portion 40 is provided with a fluorescence-image generating portion 41 that generates a fluorescence image; a white-light-image generating portion 42 that generates a white-light image (reference image); a division-image generating portion 43 that divides the fluorescence image generated by the fluorescence-image generating portion 41 by the white-light image; a corrected-image generating portion 44 that generates a corrected image by multiplying a division image generated by the division-image generating portion 43 by the fluorescence image; an identifying portion 46 that identifies regions in the corrected image that have gradation values greater than a threshold set in advance; and a combined image portion 47 that generates a combined image by superimposing the regions identified by the identifying portion 46 on the white-light image.

The fluorescence-image generating portion 41 generates a two-dimensional fluorescence image based on the fluorescence image information acquired by the fluorescence capturing portion 38, and outputs the generated fluorescence image to the division-image generating portion 43 and the corrected-image generating portion 44. Here, because a fluorescent reagent actually accumulates not only in a diseased portion but also in a healthy portion in a small amount, and because, although weaker than the fluorescence from the diseased portion, fluorescence is also emitted from the healthy portion, the generated fluorescence image is an image that has a background over the entire image (FIG. 2A).

Figure 2A:
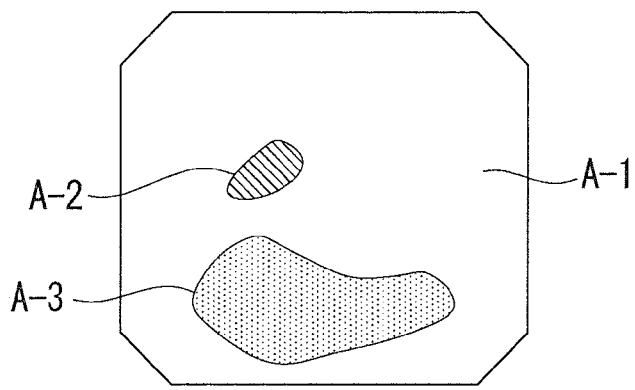
FIG. 2A is a diagram illustrating a fluorescence image generated by the fluorescence endoscope apparatus according to the first embodiment of the present invention.

Therefore, the fluorescence image includes background low-luminance regions (A-1 in FIG. 2A), regions that have relatively high luminance compared with these low-luminance regions due to the fluorescence emitted from the diseased portion (A-2 in FIG. 2A), and regions that have relatively high luminance due to the close distance to the examination target (A-3 in FIG. 2A).

The white-light-image generating portion 42 generates a two-dimensional white-light image based on the white-light image information acquired by the white-light capturing portion 39 and outputs the generated white-light image to the division-image generating portion 43 and the image combining portion 47. Here, the white-light image is an image affected by a color characteristic of the examination target, namely, the absorption characteristics of the white light (FIG. 2B).

Figure 2B:
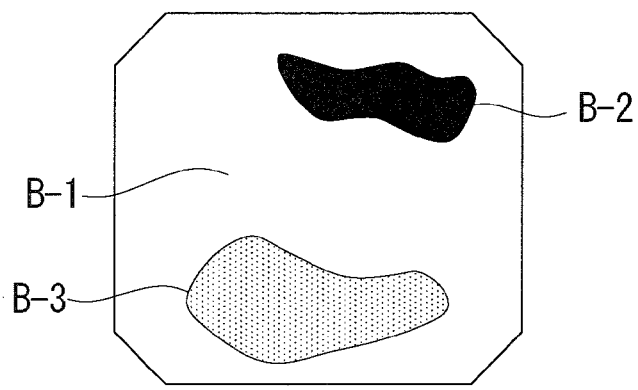
FIG. 2B is a diagram illustrating a white-light image generated by the fluorescence endoscope apparatus according to the first embodiment of the present invention.

Therefore, the generated white-light image includes background low-luminance regions due to the distribution of the reflected light over the entire image (B-1 in FIG. 2B), regions that have low luminance due to the color characteristics of the examination target (B-2 in FIG. 2B), and regions that have relatively high luminance compared with these low-luminance regions due to the close distance to the examination target (B-3 in FIG. 2B).

Figure 2C:
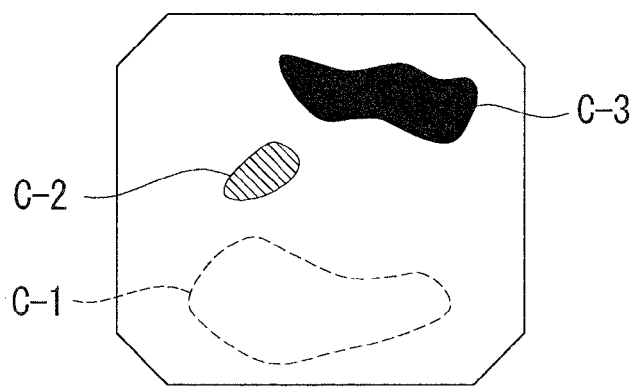
FIG. 2C is a diagram illustrating a division image generated by the fluorescence endoscope apparatus according to the first embodiment of the present invention.

The division-image generating portion 43 generates a division image by dividing the fluorescence image based on the same observation target site X by the white-light image (FIG. 2C). By doing so, it is possible to generate an image (division image) that includes regions in which the influences of the observation distance and the observation angle are reduced (C-1 in FIG. 2C).

Here, the division image includes regions that have relatively high luminance due to the fluorescence generated from the diseased portion (C-2 in FIG. 2C). Furthermore, when the white-light image includes the low-luminance regions due to the color characteristics of the examination target, high-luminance regions are included because the luminance of regions corresponding to the low-luminance regions is amplified in the division image (C-3 in FIG. 2C).

Figure 2D:
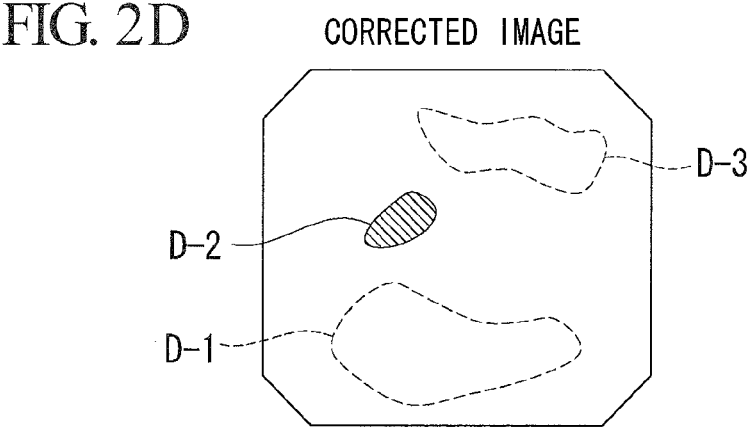
FIG. 2D is a diagram illustrating a corrected image generated by the fluorescence endoscope apparatus according to the first embodiment of the present invention.

The corrected-image generating portion 44 generates a corrected image which is a division image corrected by multiplying the division image by the fluorescence image (FIG. 2D). Here, the corrected image includes regions that reflect the results of reducing the influences of the observation distance and the observation angle in the division image (D-1 in FIG. 2D). In the corrected image, regions that are common to the regions that have relatively high luminance in the fluorescence image and the regions that have relatively high luminance in the division image are emphasized; in other words, the high-luminance regions due to the fluorescence emitted from the diseased portion are emphasized (D-2 in FIG. 2D). As a result, it is possible to generate an image (corrected image) that includes regions in which changes in the intensity of the white light due to differences in the absorption characteristics of the white light in the examination target are reduced (D-3 in FIG. 2D).

In other words, by generating a corrected image by multiplying the division image by the fluorescence image, it is possible to generate a corrected image in which, as well as suppressing the influences of the observation distance and the observation angle, even changes in the intensity of the reference light, which affect the division image, due to the differences in the absorption characteristics of the reference light in the examination target are corrected, and thus, the contrast between the fluorescence from the healthy portion (background) and that from the diseased portion is increased. Therefore, it is possible to acquire information about the examination target by suppressing the influence of the background, and it is possible to identify the diseased portion more accurately and with high precision.

Based on the threshold set in advance, the identifying portion 46 identifies, as feature regions, pixels having gradation values that are greater than the threshold among all pixels in the corrected image.

By identifying regions that have gradation values greater than the threshold in this way, it is possible to suppress the influence of weak fluorescence due to the background in the corrected image, and thus, it is possible to identify regions occupied by the diseased portion.

The combined image portion 47 generates a combined image by superimposing the feature regions identified by the identifying portion 46 on the white-light image and outputs the generated combined image to the monitor 50.

In other words, by superimposing the regions identified by the identifying portion on the reference image, it is possible to acquire a combined image having clear contrast between the regions occupied by the diseased portion and the background.

The monitor 50 displays the combined image received from the image combining portion 47.

With the thus-configured fluorescence endoscope apparatus 100, when the examination target is irradiated with the excitation light emitted from the light source, the fluorescence-image generating portion generates a fluorescence image based on the fluorescence generated at the examination target; and when the examination target is irradiated with the reference light emitted from the light source together with the excitation light, the reference-image generating portion generates a reference image based on the return light thereof. Then, at the division-image generating portion, a division image in which changes in the fluorescence intensity, which depends on the observation distance and the observation angle, are reduced is generated by dividing the fluorescence image by the reference image.

Furthermore, the corrected-image generating portion generates a corrected image in which regions that have relatively high luminance and that the division image and the fluorescence image have in common are emphasized.

Here, the division image includes background low-luminance regions, regions that have high luminance relative to these low-luminance regions because of the fluorescence emitted from the diseased portion in the fluorescence image, and regions that have relatively high luminance amplified by the division because of the color characteristics or the like of the examination target captured in the white-light image. Therefore, the regions that have relatively high luminance in the division image are regions that have luminances equal to, for example, about the top 10% to 20% in the division image, and are regions that include the high-luminance regions due to the fluorescence emitted from the diseased portion and the high-luminance regions due to the color characteristics or the like of the examination target.

In addition, the fluorescence image includes background low-luminance regions, regions that have high luminance relative to these low-luminance regions because of the fluorescence emitted from the diseased portion captured in the fluorescence image, and regions that have relatively high luminance due to the close distance to the examination target. Therefore, regions that have relatively high luminance in the fluorescence image are regions that have luminances equal to, for example, about the top 10% to 20% in the fluorescence image, and are regions that include the high-luminance regions due to the fluorescence emitted from the diseased portion and the high-luminance regions due to the distance to the examination target.

Accordingly, it is possible to generate a corrected image in which, as well as suppressing the influences of the observation distance and the observation angle, even changes in the intensity of the reference light, which affect the division image, due to the differences in the absorption characteristics of the reference light in the examination target are corrected, and thus, the contrast between the fluorescence from the healthy portion (background) and the fluorescence from the diseased portion is increased. Therefore, it is possible to acquire information about the examination target by suppressing the influence of the background, and it is possible to identify the diseased portion more accurately and with high precision.

Thus, a diseased portion can be identified more accurately and with high precision, regardless of the observation conditions and the state (color and shape) of the examination target.

Figure 3:
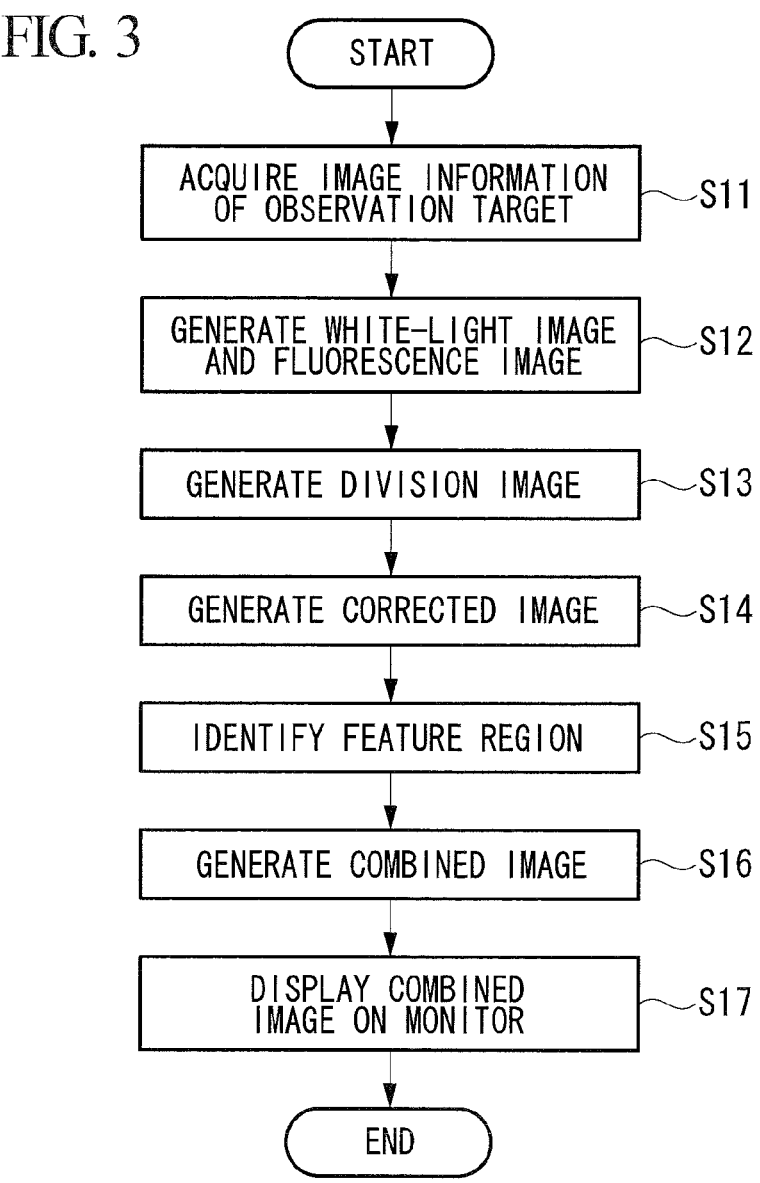
FIG. 3 is a flowchart showing the operation of the fluorescence endoscope apparatus according to the first embodiment of the present invention.

The flow for the case in which an observation target site X in a body cavity of a living organism is observed by using the thus-configured fluorescence endoscope apparatus 100 according to this embodiment will be described in accordance with a flowchart in FIG. 3.

First, to observe an observation target site X in a body cavity of a living organism by using the fluorescence endoscope apparatus 100, a fluorescent reagent that preferentially accumulates in a diseased portion, such as cancer cells or the like, is made to adhere to or to be absorbed by the observation target site X, and, subsequently, image information of the observation target site X is acquired (Step S11). In other words, in the state in which the fluorescent reagent is made to adhere to or to be absorbed by the observation target site X, the excitation light is radiated onto the observation target site X, thus generating fluorescence from the observation target site X by exciting the fluorescent reagent.

More specifically, in this embodiment, in the state in which the fluorescent reagent is made to adhere to or to be absorbed by the observation target site X, the scope 2 is inserted into the body cavity so that the distal end 2*a* faces the observation target site X. By activating the light source 10 in this state, the white light that is emitted from the xenon lamp 11 and that includes the excitation light extracted by the excitation-light filter 13 is focused by the coupling lens 15 and is guided to the distal end 2*a* of the scope 2 by the light-guide fiber 21. Then, this white light is spread out by the spreading lens 23 and is radiated onto the observation target site X.

At the observation target site X, the fluorescent substance contained therein is excited by the excitation light, thus emitting fluorescence, and, also, portions of the white light and the excitation light are reflected at the surface thereof. The fluorescence, the white light, and the excitation light are collected by the objective lens 31; light having the excitation wavelength or greater, that is, the excitation light and the fluorescence, are reflected by the beam splitter 33; and the white light whose wavelength is shorter than the excitation wavelength is allowed to pass therethrough.

The excitation-light cut filter 35 removes the excitation light from the excitation light and the fluorescence reflected by the beam splitter 33, and thus, only the fluorescence is focused by the focusing lens 37A and is captured by the fluorescence capturing portion 38. By doing so, the fluorescence capturing portion 38 acquires fluorescence image information of the observation target site X. In addition, the white light that has passed trough the beam splitter 33 is focused by the focusing lens 37B and is captured by the white-light capturing portion 39. By doing so, the white-light capturing portion 39 acquires white-light image information of the observation target site X. Note that, either the fluorescence image information or the white-light image information may be acquired first, or they may be acquired at the same time.

In the subsequent Step S12, the fluorescence image information acquired by the fluorescence capturing portion 38 and the white-light image information acquired by the white-light capturing portion 39 are respectively input to the fluorescence-image generating portion 41 and the white-light-image generating portion 42 in the image processing portion 40. At the fluorescence-image generating portion 41, a two-dimensional fluorescence image is generated based on the fluorescence image information, and the generated fluorescence image is output to the division-image generating portion 43 and the corrected-image generating portion 44. In addition, at the white-light-image generating portion 42, a two-dimensional white-light image is generated based on the white-light image information, and the generated white-light image is output to the division-image generating portion 43 and the image combining portion 47.

Note that, because the fluorescent reagent actually accumulates not only in the diseased portion but also in healthy portions in small amounts, weak fluorescence is emitted from portions other than the diseased portion (background). In addition, there are cases in which it is difficult to distinguish between a diseased portion and a healthy portion in an obtained fluorescence image because, for example, relatively high fluorescence is emitted even from a site that is healthy due to the distance and angle between the distal end 2*a* of the scope 2 and the observation target site X.

Because of this, in the subsequent Step S13, the division-image generating portion 43 generates a division image by dividing the fluorescence image by the white-light image. By doing so, it is possible to reduce changes in the fluorescence intensity in the division image, which depends on the observation distance and the observation angle. Specifically, because the intensity in the white-light image greatly depends on the observation distance and the observation angle, it is possible to reduce the influences of the observation distance and the observation angle by normalizing the fluorescence image by the white-light image. The generated division image is output to the corrected-image generating portion 44.

Here, in the white-light image, there are cases in which the inherent intensity of the reflected light cannot be obtained due to differences in the absorption characteristics of the reference light in the examination target in addition to the differences in the dependences on the observation distance and the observation angle between the fluorescence and the reflected light. Accordingly, when a division image is generated based on such a white-light image, although the influences of the changes in the fluorescence intensity due to the observation distance and the observation angle can be suppressed in the division image, there are cases in which the division image is affected by changes in the intensity of the reflected light due to the differences in the absorption characteristics of the reference light in the examination target.

Therefore, in the subsequent Step S14, the corrected-image generating portion 44 generates a corrected image in which changes in the intensity of the division image due to the differences in the absorption characteristics of the reflected light in the observation target site X are corrected by multiplying the division image by the fluorescence image. Specifically, by multiplying the division image by the fluorescence image, which is not related to absorption in the observation target site X, it is possible to generate a corrected image in which changes in the fluorescence intensity due to the observation distance and the observation angle are reduced and the influence of absorption is also reduced. More specifically, common regions between regions that have relatively high luminance in the fluorescence image and regions that have relatively high luminance in the white-light image, that is, regions in which the fluorescence is generated from the diseased portion, are emphasized in the corrected image. The generated corrected image is output to the identifying portion 46.

In the subsequent Step S15, in the corrected image input from the corrected-image generating portion 44, the identifying portion 46 identifies, based on a threshold set in advance, pixels having gradation values that are greater than the threshold among all pixels in the corrected image as feature regions, and the process advances to the subsequent Step S16. In Step S16, the combined-image generating portion 47 generates a combined image by superimposing the feature regions identified by the identifying portion 46 on the white-light image. By doing so, the contrast between the diseased portion and the background is increased in the combined image by using the predetermined threshold as a reference. The combined-image generating portion 47 outputs the generated combined image to the monitor 50. In the subsequent Step S17, the combined image received from the image combining portion 47 is displayed on the monitor 50.

As has been described above, with the fluorescence endoscope apparatus 100 according to this embodiment, by multiplying the division image generated by the division-image generating portion 43 by the fluorescence image at the corrected-image generating portion 44, the influences of the observation distance and the observation angle are suppressed, and even the changes in the intensity of the reflected light due to differences in the absorption characteristics of the reference light in the examination target, which affect the division image, are corrected, thus making it possible to generate the corrected image in which the contrast between the fluorescence from the healthy portions (background) and the diseased portion is increased.

Furthermore, because regions that have gradation values greater than the threshold, which mainly indicate the fluorescence from the diseased portion, are identified by the identifying portion as the feature regions, by generating the combined image by superimposing these feature regions on the white-light image, the contrast between the diseased portion and the background is further increased in the generated combined image by using the threshold as a reference. Therefore, the diseased portion can be identified more accurately and with high precision in the corrected image in which the influences that that background exerts on the division image depending on the changes in the reference light intensity due to the absorption characteristics in the examination target are suppressed.

Note that, when generating the corrected image in this embodiment, the division image is generated first, and this division image is multiplied by the fluorescence image; however, the sequence of the calculations is not limited thereto, and possible calculation sequences include, for example, a sequence in which the fluorescence image is multiplied by the fluorescence image followed by division by the white-light image.

Modification of the First Embodiment

In addition, this embodiment may be modified as described below.

Figure 4:
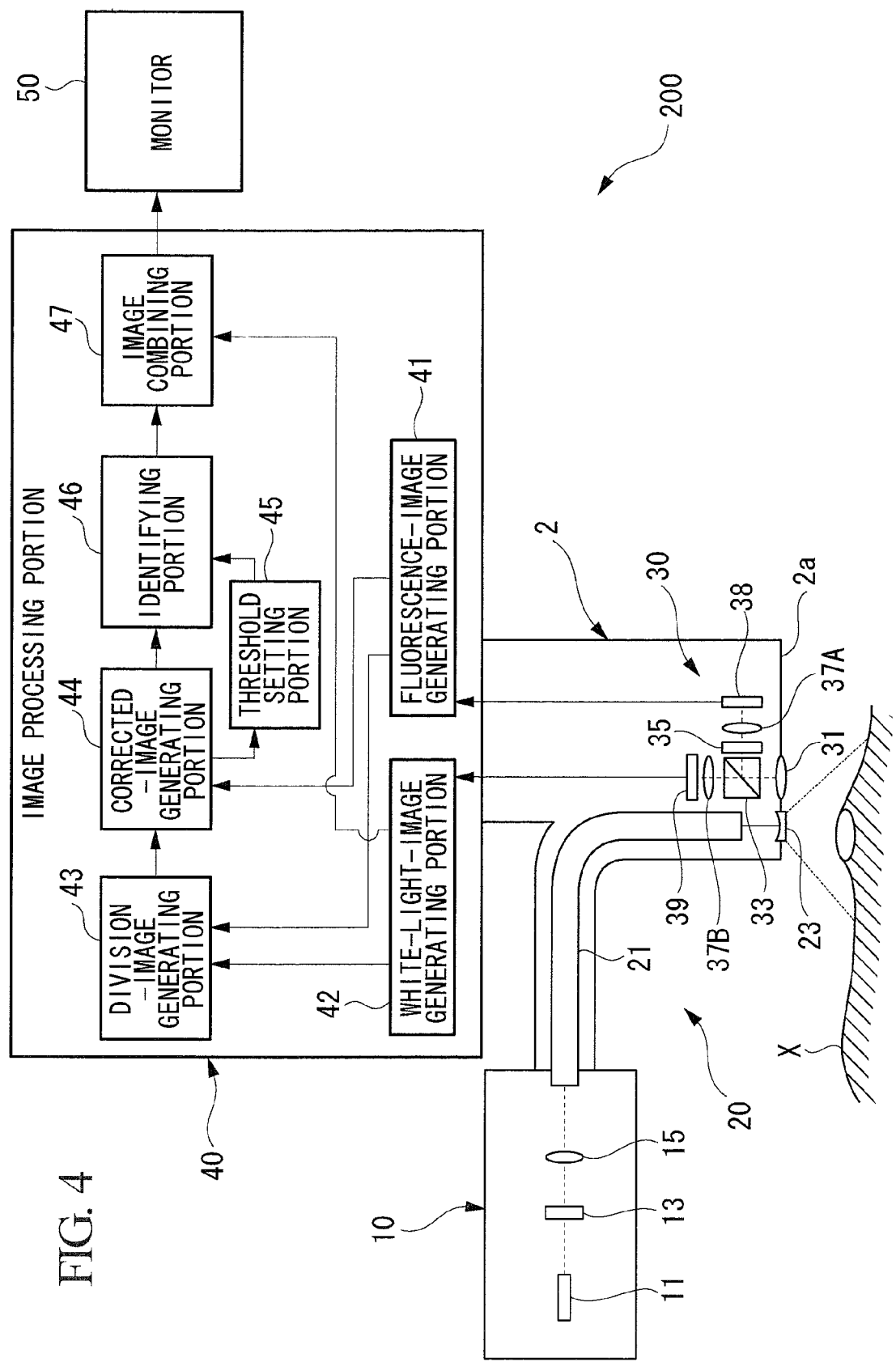
FIG. 4 is a diagram showing, in outline, the configuration of a fluorescence endoscope apparatus according to a modification of the first embodiment of the present invention.

With the fluorescence endoscope apparatus 100 according to the first embodiment described above, the identifying portion 46 identifies regions that have gradation values greater than the threshold set in advance in the corrected image; however, there is no limitation thereto, and it is possible to modify the above-described embodiment as in a fluorescence endoscope apparatus 200 shown in FIG. 4. Specifically, the configuration of the fluorescence endoscope apparatus 200 in FIG. 4 includes a threshold setting portion 45 that acquires information about the corrected image from the corrected-image generating portion 44 and computes and sets a threshold based on this corrected image. The fluorescence endoscope apparatus 200 according to this modification will be described below.

Note that, as shown in FIG. 4, the difference between the fluorescence endoscope apparatus 200 according to this modification and the fluorescence endoscope apparatus 100 according to the first embodiment described above is that the threshold setting portion 45 is additionally provided, and, because other configurations are common between the two apparatuses, the same reference signs are assigned to the common configurations, and the descriptions thereof will be omitted.

The fluorescence endoscope apparatus 200 is provided with the threshold setting portion 45 that computes and sets a threshold that serves as a reference when the identifying portion 46 identifies the feature regions. The threshold setting portion 45 acquires information about the corrected image from the corrected-image generating portion 44 and computes and sets the threshold based on the average value of gradation values of the individual pixels in this corrected image. More specifically, as shown in the following Expression (1), the threshold setting portion 45 sets a value obtained by multiplying an average gradation value m for the entire corrected image by a predetermined factor a as a threshold S, and outputs the set threshold S to the identifying portion 46.

$$S = am \quad (1)$$

By setting the threshold based on the average value of gradation values of individual pixels in the corrected image in this way, even in the case in which there is variability in the average values of the gradation values of the individual pixels among images, it is possible to set a more precise threshold, and thus, it is possible to identify the regions occupied by the diseased portion more accurately.

Figure 5:
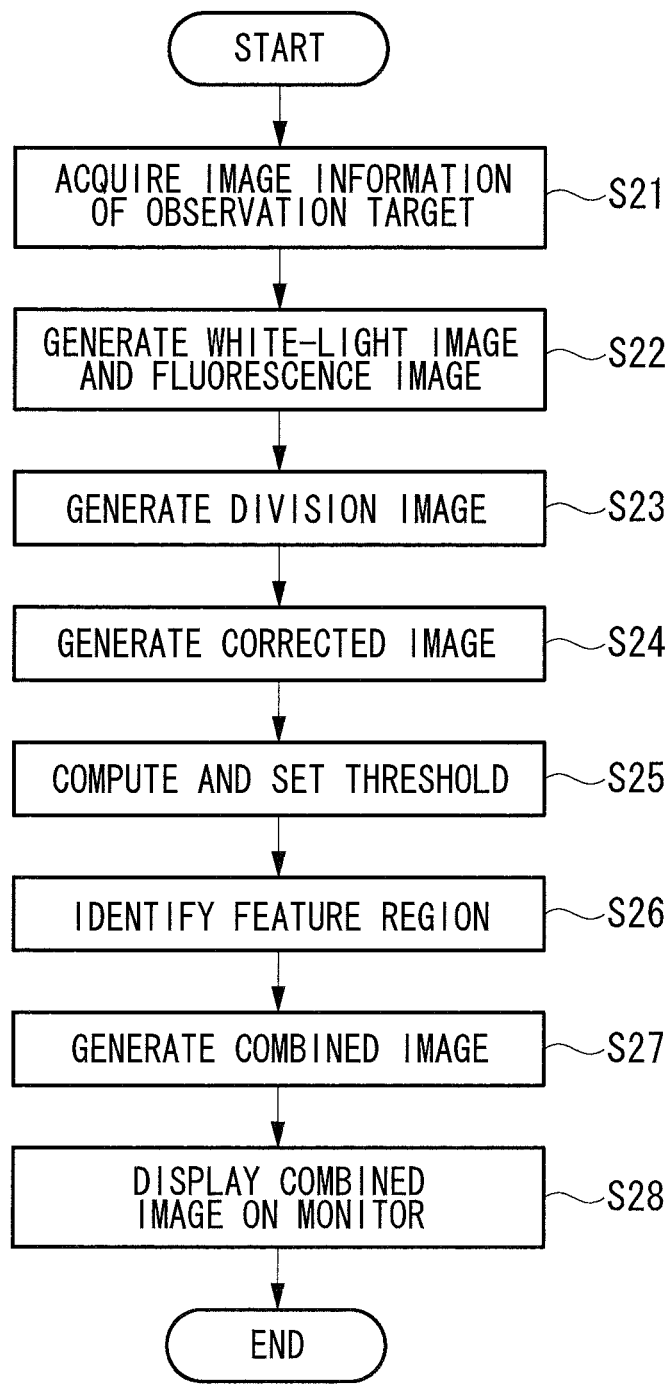
FIG. 5 is a flowchart showing the operation of the fluorescence endoscope apparatus according to the modification of the first embodiment of the present invention.

The flow for the case in which an observation target site X in a body cavity of a living organism is observed by using the thus-configured fluorescence endoscope apparatus 200 according to this modification will be described in accordance with a flowchart in FIG. 5.

As with the fluorescence endoscope apparatus 100 according to the first embodiment described above, the fluorescence endoscope apparatus 200 according to this modification acquires image information of the observation target site X, generates a fluorescence image and a white-light image, and generates a division image and a corrected image based on the fluorescence image and the white-light image (Steps S21 to S24). The generated corrected image is output to the threshold setting portion 45 and is also output to the identifying portion 46, and the process advances to the subsequent Step S25.

In Step S25, at the threshold setting portion 45, in addition to determining the factor a in the above-described Expression (1), the average gradation value m for the entire image is calculated from the corrected image output from the image correcting portion 43, and the threshold S is calculated by using the set factor a and the calculated average gradation value m for the entire image based on Expression (1). By doing so, the threshold S is set for the gradation value of the corrected fluorescence image, and the set threshold S is output to the identifying portion 46.

In the subsequent Step S26, by using the threshold S set in Step S25 as a reference, the identifying portion 46 identifies, from the corrected image, pixels having gradation values greater than the threshold S among all pixels in this corrected image as feature regions, and the process advances to the subsequent Step S27. In Step S27, the combined-image generating portion 47 generates a combined image by superimposing the feature regions identified by the identifying portion 46 on the white-light image. By doing so, the contrast between the diseased portion and the background is increased in the combined image by using the predetermined threshold as a reference. The combined-image generating portion 47 outputs the generated combined image to the monitor 50. In the subsequent Step S28, the combined image received from the image combining portion 47 is displayed on the monitor 50.

As has been described above, with the fluorescence endoscope apparatus 200 according to this modification, in addition to the advantage of the fluorescence endoscope apparatus 100 according to the first embodiment, because the identifying portion additionally identifies the regions that have gradation values greater than the threshold, which mainly indicate the fluorescence from the diseased portion, as the feature regions, by generating the combined image by superimposing these feature regions on the white-light image, the contrast between the diseased portion and the background is further increased in the generated combined image by using the threshold as a reference. In particular, because the threshold setting portion sets the threshold based on the average gradation value for the entire corrected image, it is possible to update the threshold in accordance with the fluctuations in the gradation values in the corrected image, to reduce the influence in the acquired corrected image due to individual differences among examination targets and changes over time occurring therein, and to identify the diseased portion with high precision. Therefore, it is possible to acquire information about the observation target site X by suppressing the influence of the background, and thus, it is possible to identify the diseased portion more accurately and with high precision.

Note that, in this modification, the threshold is set based on the average gradation value m; however, there is no limitation thereto, and, for example, the threshold S may be set based on a sum of the average gradation value m for the entire image and a standard deviation σ, as shown in Expression (2) below:

$$S = m + b\sigma \quad (2),$$

where σ is the standard deviation of gradation values of the individual pixels in the corrected image.

In this case, even in the case in which there is variability among the gradation values of the individual pixels in the corrected image, it is possible to set a highly precise threshold as compared with the case in which the threshold is set based only on the average gradation value.

In addition, the threshold setting portion may set the threshold for each corrected fluorescence image in subsequent frames, and the threshold may also be set when the average values of the gradation values of the individual pixels in subsequent frames change in excess of a certain proportion.

Second Embodiment

Next, a second embodiment of the present invention will be described.

In describing this embodiment, the same reference signs are assigned to the configurations common with the fluorescence endoscope apparatus 100 according to the first embodiment described above, and the descriptions thereof will be omitted.

Figure 6:
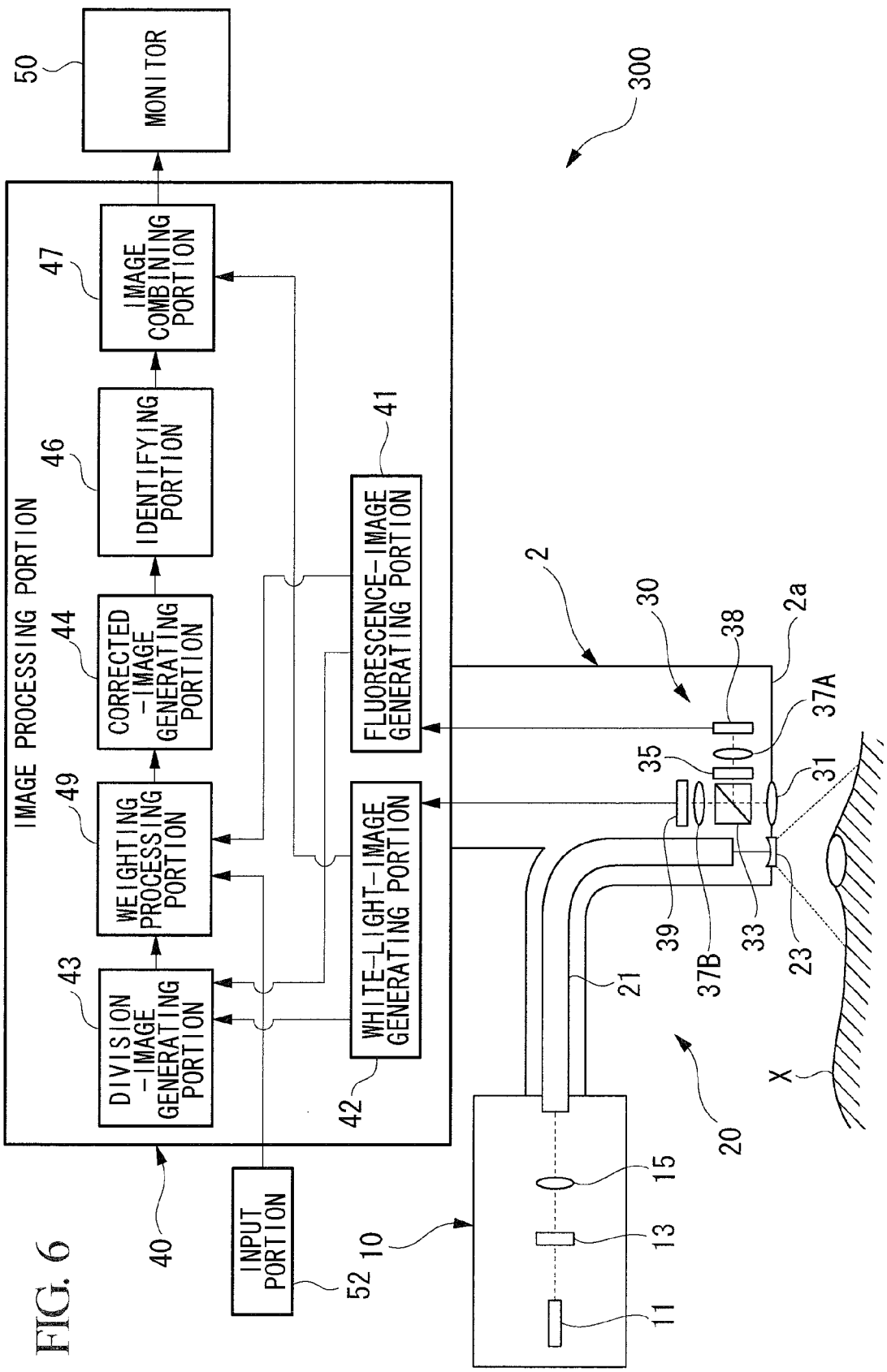
FIG. 6 is a diagram showing, in outline, the configuration of a fluorescence endoscope apparatus according to a modification of a second embodiment of the present invention.

In the fluorescence endoscope apparatus 100 according to the first embodiment, the corrected-image generating portion 44 generates the corrected image by multiplying the division image by the fluorescence image; however, with a fluorescence endoscope apparatus 300 according to this embodiment, the configuration of this embodiment is such that weights are assigned to the division image and the fluorescence image before generating the corrected image, as shown in FIG. 6.

Specifically, the fluorescence endoscope apparatus 300 in FIG. 6 is provided with an input portion 52 for inputting information related to the examination target, and a weighting processing portion 49 that acquires information about the corrected image from the division-image generating portion 43 and also acquires information about the examination target from the input portion 52 to assign predetermined weights to the division image and the fluorescence image.

The information related to the observation target site X is stored in advance in the input portion 52. In a living organism that serves as the examination target, conditions greatly differ depending on the observation site, including cases in which the color of the observation target site is complex because various types of tissue are included as in an abdominal cavity, as well as cases in which the tissue thereof is uniform, as in an internal wall or the like of the digestive tract, thus having nearly uniform color in the observation target site. When the color of the observation target site is complex, it tends to be difficult to determine a diseased portion in a division image because the fluorescence intensity of healthy portions may be increased when displayed. On the other hand, when the color of the observation target site is substantially uniform, because the absorption characteristics of white light becomes substantially uniform, the influence exerted by the color characteristics of the examination target on the division image becomes relatively small. Therefore, the input portion 52 is provided with, for example, a table for recording, as the information related to the observation target site X, whether individual sites in a living organism belong to an observation-target-site group having complex color or belong to an observation-target-site group having substantially uniform color.

The weighting processing portion 49 performs two kinds of weighting processing for the division image acquired from the division-image generating portion 43 and the fluorescence image acquired from the fluorescence-image generating portion 41, depending on whether the observation target site X belongs to the observation-target-site group having complex color or belongs to the observation-target-site group having substantially uniform color. Specifically, based on the information related to the observation target site X acquired from the input portion 52, the weighting processing is performed so as to assign weight to the fluorescence image when the observation target site X belongs to the observation-target-site group having complex color. On the other hand, the weighting processing is performed so as to assign weight to the division image when the observation target site X belongs to the observation-target-site group having substantially uniform color. The weighting processing portion 49 outputs the division image subjected to the weighting processing and the white-light image subjected to the weighting processing to the corrected-image generating portion 44.

The corrected-image generating portion 44 generates a corrected image by adding the division image subjected to the weighting processing and the fluorescence image subjected to the weighting processing, which are acquired from the weighting processing portion 49.

Note that, although the case of addition is described as an example of the weighting processing, there is no limitation thereto, and, for example, the weight may be assigned by using A and B as weighting factors in (division image)^A× (fluorescence image)^B, or by using other computational processing, namely, multiplication, addition, exponentiation, and so forth, separately or in an appropriate combination.

With the weighting processing portion 49, it is possible to obtain a corrected image with greater precision. Therefore, it is possible to acquire the information about the examination target by suppressing the influence of the background, and it is possible to identify the diseased portion more accurately and with high precision.

Figure 7:
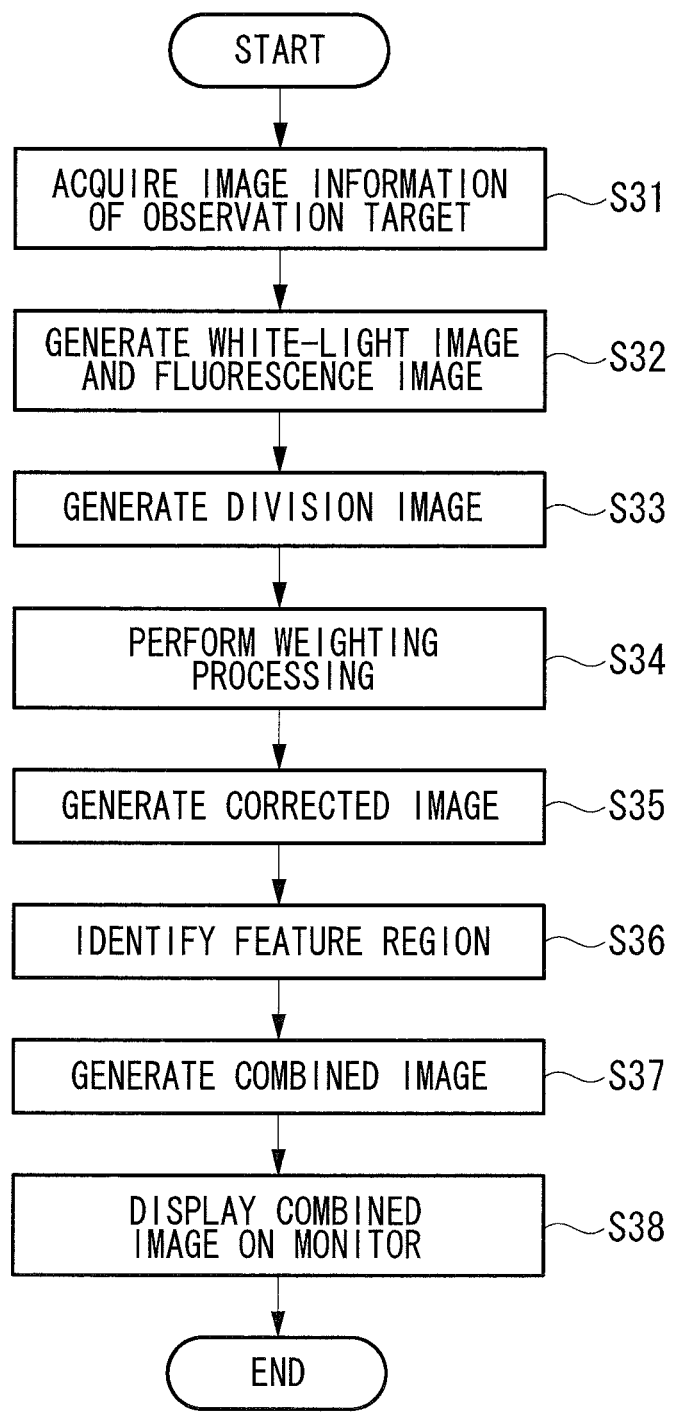
FIG. 7 is a flowchart showing the operation of the fluorescence endoscope apparatus according to the second embodiment of the present invention.

The flow for the case in which an observation target site X in a body cavity of a living organism is observed by using the thus-configured fluorescence endoscope apparatus 300 according to this embodiment will be described in accordance with a flowchart in FIG. 7.

As with the fluorescence endoscope apparatus 100 according to the first embodiment described above, the fluorescence endoscope apparatus 300 according to this embodiment acquires image information of the observation target site X, generates a fluorescence image and a white-light image, and generates a division image based on the fluorescence image and the white-light image (Steps S31 to S33). The generated division image is output to the weighting processing portion 49, and the process advances to the subsequent Step S34.

In Step S34, for example, when an operator of the fluorescence endoscope apparatus 300 inputs information for specifying the observation target site X to the input portion 52, a selection is made with reference to the table stored in the input portion 52 regarding which observation-target-site groups the observation target site X belongs to, and the input portion 52 outputs the information related to the selected observation target site X to the weighting processing portion 49. At the weighting processing portion 49, the weighting processing is performed based on the information related to the observation target site X acquired from the input portion 52 so as to assign weight to the fluorescence image when the observation target site X belongs to the observation-target-site group having complex color and, on the other hand, so as to assign weight to the division image when the observation target site X belongs to the observation-target-site group having substantially uniform color. The division image and the fluorescence image subjected to the weighting processing are output to the corrected-image generating portion 44.

In the subsequent Step S35, by adding the division image subjected to the weighting processing and the fluorescence image subjected to the weighting processing, which are acquired from the weighting processing portion 49, a corrected image in which the changes in the fluorescence intensity in the division image due to the observation distance and the observation angle and the changes in the intensity of the reflected light due to the differences in the absorption characteristics of the reflected light in the observation target site X are corrected is generated. The generated corrected image is output to the identifying portion 46.

In the corrected image input from the corrected-image generating portion 44, the identifying portion 46 identifies, based on the threshold set in advance, pixels having gradation values that are greater than the threshold among all pixels in the corrected image as feature regions, and the combined-image generating portion 47 generates a combined image by superimposing these feature regions on the white-light image (Steps S36 to S37). By doing so, the contrast between the diseased portion and the background is increased in the combined image by using the predetermined threshold as a reference. The combined-image generating portion 47 outputs the generated combined image to the monitor 50. In the subsequent Step S38, the combined image received from the image combining portion 47 is displayed on the monitor 50.

As has been described above, with the fluorescence endoscope apparatus 300 according to this embodiment, in addition to the advantage of the fluorescence endoscope apparatus 100 according to the first embodiment, because it is possible to generate a corrected image in accordance with the observation target site by adding the fluorescence image to the division image by means of the corrected-image generating portion 44 after assigning weights to the division image and the fluorescence image in accordance with the observation target site by means of the weighting processing portion 49, it is possible to identify the diseased portion more accurately and with high precision by suppressing the influence of the background.

In other words, by generating a corrected image by adding the fluorescence image to the division image, it is possible to generate a corrected image in which, as well as suppressing the influences of the observation distance and the observation angle, even changes in the intensity of the reference light, which affect the division image, due to the differences in the absorption characteristics of the reference light in the examination target are corrected, and thus, the contrast between the fluorescence from the healthy portion (background) and that from the diseased portion is increased. Therefore, it is possible to acquire information about the examination target by suppressing the influence of the background, and it is possible to identify the diseased portion more accurately and with high precision.

Note that, the configuration of this embodiment is such that two kinds of weighting processing are performed depending on whether the observation target site X belongs to the observation-target-site group having complex color or belongs to the observation-target-site group having substantially uniform color; however, there is no limitation thereto, and, for example, it is possible to employ a configuration in which different weighting processing is performed for separate observation target sites.

In addition, the information for specifying the observation target site X input by the operator is used to judge whether the observation target site X belongs to the observation target site group having complex color or belongs to the observation target site group having substantially uniform color; however, methods such as a method in which a judgment is automatically made based on the color variability in the white-light image may be employed.

In addition, this embodiment can be modified as described below.

With the fluorescence endoscope apparatus according to the second embodiment described above, the weighting processing is performed after generating the division image; however, a subtraction processing portion may be provided, which subtracts noise signals (signals that are minimally detected due to the characteristics of the examination target or signals that are inevitably generated due to the characteristics of the observation system) from one of or individually from both the division image and the fluorescence image before performing the weighting processing.

For example, instead of the above-described Step S33, the subtraction processing portion may generate subtracted images in which the noise is subtracted from the fluorescence image and the division image, respectively (Step S33'). A corrected image is generated by performing the weighting processing on the generated subtracted images.

By doing so, by reducing the influence of the background, which is the fluorescence from the healthy portions, it is possible to obtain a corrected image in which the contrast between the fluorescence from the healthy portions and the diseased portion is increased even more. Therefore, it is possible to identify the diseased portion more accurately and with high precision.

In addition, although the weighting processing is performed after generating the subtracted images in this modification, the corrected image may be generated without assigning weight.

Note that, it is also possible to employ a configuration in which scope information is used to specify the observation target site X. Specifically, the fluorescence endoscope apparatus may be provided with an attachable/detachable scope including an IC chip that stores the scope information, and the light source 10 may be provided with a scope distinguishing portion that distinguishes the scope information stored in the IC chip. Examples of the scope information include information related to observation target sites corresponding to respective scopes and so forth.

In this case, when a scope is connected to the light source 10, the scope distinguishing portion reads out the scope information stored in the IC chip thereof, the information is transmitted to the input portion, and the observation target site is specified based on the scope information. Then, the information related to the specified observation target site is output to the weighting processing portion.

Although the above-described embodiment has been described based on the color characteristics of the examination target, a similar advantage can be afforded even in the case in which the intensity of the return light is reduced due to factors other than distance (for example, the shape, such as depressions and protrusions).

REFERENCE SIGNS LIST 10 light source
41 fluorescence-image generating portion
42 white-light-image generating portion
43 division-image generating portion
44 corrected-image generating portion
45 threshold setting portion
46 identifying portion
47 image combining portion
49 weighting processing portion
50 monitor
52 input portion
100 fluorescence endoscope apparatus
200 fluorescence endoscope apparatus
300 fluorescence endoscope apparatus

The invention claimed is:

1. A fluorescence endoscope apparatus comprising:
a light source configured to radiate excitation light and reference light onto an examination target;
a fluorescence-capturing sensor configured to acquire fluorescence image information by capturing fluorescence generated by the examination target due to irradiation with the excitation light from the light source;
a white-light capturing sensor configured to acquire white light information by capturing return light that returns from the examination target due to irradiation with the reference light from the light source; and
a processor comprising hardware, wherein the processor is configured to:
generate a fluorescence image based on the fluorescence image information;
generate a reference image based on the white light information;
generate a division image by dividing the fluorescence image by the reference image; and
generate a corrected image by multiplying the division image by the fluorescence image.

2. The fluorescence endoscope apparatus according to claim 1,
wherein the processor is further configured to:
perform a subtraction processing on the division image and/or the fluorescence image in accordance with the examination target; and
generate the corrected image based on the division image and/or the fluorescence image subjected to the subtraction processing.

3. The fluorescence endoscope apparatus according to claim 2,
wherein the processor is further configured to:
after performing the subtraction processing, perform a weighting processing on the division image and the fluorescence image in accordance with the examination target.

4. The fluorescence endoscope apparatus according to claim 1,
wherein the processor is further configured to:
perform a weighting processing by assigning weights to the division image and the fluorescence image in accordance with the examination target; and
generate the corrected image based on the division image and the fluorescence image subjected to the weighting processing.

5. The fluorescence endoscope apparatus according to claim 1,
wherein the processor is configured to:
identify, a region that has a gradation value greater than a predetermined threshold in the corrected image.

6. The fluorescence endoscope apparatus according to claim 5,
wherein the processor is configured to:
set the predetermined threshold based on an average value of gradation values of individual pixels in the corrected image.

7. The fluorescence endoscope apparatus according to claim 5,
wherein the processor is configured to:
generate a combined image by superimposing the region that has the gradation value greater than the predetermined threshold in the corrected image on the reference image.

8. A fluorescence endoscope apparatus comprising:
a light source configured to radiate excitation light and reference light onto an examination target;
a fluorescence-capturing sensor configured to acquire fluorescence image information by capturing fluorescence generated by the examination target due to irradiation with the excitation light from the light source;
a white-light capturing sensor configured to acquire white light information by capturing return light that returns from the examination target due to irradiation with the reference light from the light source; and
a processor comprising hardware, wherein the processor is configured to:
generate a fluorescence image based on the fluorescence image information;
generate a reference image based on the white light information;
generate a division image by dividing the fluorescence image by the reference image; and
generate a corrected image by adding the division image and the fluorescence image.

9. The fluorescence endoscope apparatus according to claim 8,
wherein the processor is configured to:
perform a subtraction processing on the division image and/or the fluorescence image in accordance with the examination target; and
generate the corrected image based on the division image and/or the fluorescence image subjected to the subtraction processing.

10. The fluorescence endoscope apparatus according to claim 9,
wherein the processor is configured to:
after performing the subtraction processing, perform a weighting processing on the division image and the fluorescence image in accordance with the examination target.

11. The fluorescence endoscope apparatus according to claim 8,
wherein the processor is configured to:
perform a weighting processing by assigning weights to the division image and the fluorescence image in accordance with the examination target; and
generate the corrected image based on the division image and the fluorescence image subjected to the weighting processing.

12. The fluorescence endoscope apparatus according to claim 8,
wherein the processor is configured to:
identify, a region that has a gradation value greater than a predetermined threshold in the corrected image.

13. The fluorescence endoscope apparatus according to claim 12,
wherein the processor is configured to:
set the predetermined threshold based on an average value of gradation values of individual pixels in the corrected image.

14. The fluorescence endoscope apparatus according to claim 12,
wherein the processor is configured to:
generate a combined image by superimposing the region that has the gradation value greater than the predetermined threshold in the corrected image on the reference image.

* * * * *